United States Patent [19]
Guadagno et al.

[11] Patent Number: 5,171,410
[45] Date of Patent: Dec. 15, 1992

[54] METHOD AND FORMULATION FOR CREATING KINASE ISOFORM SEPARATION

[75] Inventors: Philip A. Guadagno, Vidor; Aungnapa Tansamrit; Subphong Tansamrit, both of Beaumont, all of Tex.

[73] Assignee: Helena Laboratories Corporation, Beaumont, Tex.

[21] Appl. No.: 424,104

[22] Filed: Oct. 20, 1989

[51] Int. Cl.$^5$ ............................................. G01N 27/26
[52] U.S. Cl. ............................. 204/182.8; 204/299 R
[58] Field of Search ......................... 204/182.8, 299 R

[56] References Cited

U.S. PATENT DOCUMENTS

| | | | |
|---|---|---|---|
| 3,932,221 | 1/1976 | Pfleider | 195/103.5 R |
| 4,900,662 | 2/1990 | Shah | 435/7 |
| 4,945,044 | 7/1990 | Huszar | 435/17 |
| 5,006,473 | 4/1991 | Bourma et al. | 436/512 |

OTHER PUBLICATIONS

The Journal of Biological Chemistry, vol. 263, No. 32, Nov. 15, 1988, pp. 16963-16969, "Mitochondrial Creatine Kinase from Cardiac Muscel and Brain Are". . . Form Octameric Molecules, Schlegel et al.
Clinical Chemistry, vol. 34, No. 3, 1988, pp. 489-492, "Stability and Electrophoretic Characteristics of Creatine Kinase BB Extracted from Human Brain and Intestine", Chastain et al.
7-Enzymes, vol. 108, 1988, p. 243.
7-Enzymes, vol. 102, No. 5, 4. Feb. 1985, p. 237.
13-Mammalian Biochem., vol. 105, 1986, p. 475.
Chemical Abstracts, vol. 105, 1986, p. 476.
Chemical Abstracts, vol. 106, 1987, p. 272.
Sensitive, Rapid Assays of Subforms of Creatine Kinase MB in Plasma, Clin. Chem. 35/7, 1452-1455 (1987).
Gorus et al., "A Sensitive Bioluminescent Immunoinhibition Test for CK-B Subunit Activity and a CK-MB Specific Elisa Compared; Correlation with Agarose Electrophoresis and Influence of CK-Isoenzyme Profile on Results," Clinical Chemistry, vol. 34, No. 7, pp. 1474-1478 (1988).
Puleo et al., "Sensitive Rapid Assay of Subforms of Creatine Kinase MB in Plasma" Clinical Chemistry, vol. 35, No. 7, pp. 1492-1495 (1989).

*Primary Examiner*—John Niebling
*Assistant Examiner*—David G. Ryser
*Attorney, Agent, or Firm*—Spencer, Frank & Schneider

[57] ABSTRACT

An improved gel formulation and method for high-voltage, short duration electrophoretic separation of isoforms of CK isoenzymes. The gel is an homogeneous mixture of agarose and a buffer having a molarity of about 0.05M. CK-MM and/or CK-MB isoforms are electrophoretically separated.

11 Claims, No Drawings

METHOD AND FORMULATION FOR CREATING KINASE ISOFORM SEPARATION

BACKGROUND OF THE INVENTION

This invention relates to a method and formulation for creatine kinase separation by electrophoresis. More specifically, the present invention relates to a method and formulation for separation of creatine kinase isoforms by electrophoresis.

Creatine kinase or CK is a known enzyme, and CK activity has been found in several human tissues, the major sources being skeletal muscles, myocardium and brain. There are two creatine kinase subunits, M and B, which combine to form the three CK isoenzymes which may be found in human serum. These isoenzymes are dimers composed of the two subunits and have been identified as CK-BB, CK-MB and CK-MM. These three isoenzymes have also been referred to as CK-1, CK-2 and CK-3 based upon their relative degrees of movement during electrophoretic separation, CK-1 being the most anodal, CK-2 being less anodal and CK-3 being the least anodal. The CK-1 or CK-BB isoenzyme is found predominantly but not exclusively in brain tissue, the CK-3 or CK-MM isoenzyme is found predominantly but not exclusively in skeletal muscle, and the CK-2 or CK-MB isoenzyme is found predominantly but not exclusively in the myocardium.

CK isoenzyme testing, typically performed by electrophoresis, is a specific and reliable procedure frequently used to aid in the diagnosis of myocardial infarction.

Isoforms, also known as subtypes, subforms or isomers, are variants of CK-MM and CK-MB isoenzymes with different isoelectric points. Prior to the present invention, several investigators have reported that the CK-3 or CK-MM isoenzyme can be further broken down into as many as five isoforms which can be found by isoelectric focusing or column chromatofocusing techniques. CK-3 or CK-MM has been shown to be a dimer of two identical peptide chains containing a carboxy terminal lysine which serves as a substrate for serum carboxypeptidase. This particular chemical composition comprises one of the three major isoforms of CK-3. The removal of a lysine by a serum carboxypeptidase creates a more anodal migrating band during electrophoresis and comprises the second major isoform. The third isoform occurs when the terminal lysine is removed from the second peptide chain. This third isoform band migrates even more anodally than the other forms.

Utilizing the nomenclature system wherein the most anodal band is given the numeral 1, then among the isoforms of CK-MM (CK-3), the most anodal isoform would be CK-$3_1$, the next most anodal would be CK-$3_2$, and the next most anodal would be CK-$3_3$, etc. The clinical significance appears to be, at the present time, that the actual length of time that CK has been released into the serum may be estimated by comparing the relative amounts of the CK isoforms present. Thus, the CK-$3_3$ to CK-$3_1$ ratio analysis gives an earlier indication of acute myocardial infarction then the mere presence of CK-2 heretofore relied upon. The ratio analysis has also been used during investigational or research procedures to monitor the effect of thrombolytic therapy and to document the time of myocardial occlusion onset more accurately.

Prior to the present invention it has also been reported that CK-2 or CK-MB is a dimer of one M subunit and one B subunit which can be further broken down into two isoforms where only the M subunit contains a carboxy terminal lysine. The removal of the lysine by a serum carboxypeptidase creates a more anodal migrating band during electrophoretic separation. Again using the nomenclature system where the most anodal band is given the numeral 1, then the isoforms of CK-MB (CK-2) would be identified as CK-$2_1$ and CK-$2_2$, with CK-$2_1$ being the more anodal.

Prior to the present invention, however, CK-MM isoform separation has been obtained primarily by isoelectric focusing, by column chromatography or by cellulose acetate electrophoresis all of which are time consuming such that the results are not usually available to permit treatment on a real time basis. Furthermore, prior to the present invention, CK-MB isoform separation had been achieved primarily by isoelectric focussing or by column chromatography.

SUMMARY OF THE INVENTION

The present invention provides for the rapid, accurate, reproducible CK-MM and CK-MB isoform separation utilizing an improved agarose electrophoretic method, formulation and system. The present invention provides for accurate, consistent, reproducible CK-MM and CK-MB isoform separation by electrophoresis using an improved electrophoretic gel comprising agarose and buffer, preferably as an homogeneous mixture to which may be added humectants, stabilizers and preservatives (as is conventional in agarose electrophoretic separation gels). The present invention provides an improved electrophoretic method for such separation including the use of a high-voltage gradient, for a short time duration, to achieve the desired CK-MM and CK-MB isoform separation.

The CK-$2_2$ to CK-$2_1$ ratio analysis appears to be an even earlier indication of acute myocardial infarction than the CK-$3_3$ to CK-$3_1$ ratio analysis.

DETAILED DESCRIPTION OF THE INVENTION

By way of further background, prior to explaining the details of the present invention, it should be appreciated that CK separation into the three major isoenzyme bands CK-1, CK-2 and CK-3 (CK-BB, CK-MB and CK-MM, respectively) by electrophoretic separation is, of course, well known.

Electrophoresis is well understood as the movement of charged molecules on a medium under the influence of an electric field. Common, well-known media for electrophoretic separation are paper, agarose, cellulose acetate and acrylamide gel. Electrophoresis also includes the use of a buffer as is conventional.

Prior to the present invention, the separation of CK into the CK-MM, CK-MB and CK-BB fractions or isoenzymes was performed using either a cellulose acetate plate or an agarose gel. For example, Helena Laboratories Corporation, the assignee of the present invention, manufactured and sold the components for CK isoenzyme electrophoresis on agarose plates utilizing an AMP buffer prior to the present invention. Helena Laboratories also has marketed a cellulose acetate plate (as contrasted to an agarose gel) which has been used for CK isoform electrophoretic separation prior to the present invention.

The present invention may be expeditiously utilized in the REP (Rapid ElectroPhoresis) automated system manufactured and sold by Helena Laboratories Corporation in which the REP gel, an homogeneous mixture of agarose and buffer, is cast in a gelatinous form. The basic principles of an homogeneous cast gel including agarose, per se, and a buffer, per se, is described more fully in the copending application of Sarrine, et al., application Ser. No. 07/074,584, filed Jul. 17th, 1987, for Electrophoresis Plate and Method of Making Same, assigned to Helena Laboratories Corporation, the disclosure of which is hereby incorporated by reference.

The present invention provides for CK-MM isoform separation using a REP system where the agarose gel plate includes the following preferred homogeneous mixture:

| INGREDIENT | MINIMUM | OPTIMUM | MAXIMUM |
| --- | --- | --- | --- |
| Tris | 3.07 | 3.42 | 3.76 |
| Barbital | 3.6 | 4.0 | 4.4 |
| Sodium Azide | 0.09 | 0.10 | 0.11 |
| EDTA | 0.31 | 0.35 | 0.38 |
| Sucrose | 90 | 100 | 110 |
| Agarose | 7.2 | 8 | 8.8 |
| Sephadex | 0.9 | 1.0 | 1.1 |

The data given in the above table is set forth in grams per liter. Further information and identification of the above ingredients will now be provided. The Tris is a 2-amino-2(hydroxymethyl)-1,3-propandiol such as Trizma sold by Sigma Chemicals. Tris is also referred to as a tris amine buffer. Barbital is a barbituric acid and, more specifically, a 5,5-diethyl barbituric acid. The Tris and Barbital together form a buffer having a molarity from about 0.045M to about 0.055M, preferably about 0.050M. If separation of CK-MM into its isoforms is desired, the final gel or system pH should be alkaline, in the range of about 7.9 to about 8.5 with a pH of about 8.2 preferred. The EDTA (ethylenediamine tetraacetic acid) is preferably provided in the tetrasodium form and functions in a common manner as a general stabilizer for the gel to increase the ionic strength without changing the pH of the system. The use of EDTA for this purpose in electrophoretic separation is well known. The sodium azide is utilized as a preservative, and this use is also well known in electrophoretic gels. The sucrose functions as a humectant to keep moisture in the plate and to increase the resistance of the gel, and this function of sucrose is also well documented for use in electrophoretic gels.

The agarose gel utilized is manufactured by FMC under the trademark Isogel and has been marketed for isoelectric focusing because of its low electroendosmotic properties. Sephadex is Pharmacia's trademark for an anion exchange resin containing quaternary ammonium groups. As a preferred alternative, agarose gel manufactured by FMC under the designation HGT(P), which refers to high gel temperature, a purified gel, may be utilized in an amount of 12 grams per liter optimum, with a range of 10.8 to 13.2 grams per liter. Furthermore, a preferred agarose gel would include a cap on the gel buffer blocks, the cap made of Isogel and Sephadex mixture each in the amount of 18 grams per liter optimum and each with a range of 16.2 to 19.8 grams per liter. The buffer block cap, which is also referred to as a laminated gel block, is more fully disclosed in copending application of Tansamrit, et al., application Ser. No. 07/313,764, filed Feb. 22, 1989, for Electrophoresis Plate and Method of Making Same, assigned to Helena Laboratories Corporation, the assignee of the present invention, the disclosure of which is hereby incorporated by reference.

The foregoing formulation provides primarily CK-MM separation. If it is desired to provide primarily CK-MB separation, the system should be modified to be acidic and to have a pH in the range of about 5.9 to about 6.5 with about 6.2 preferred. For this purpose, while maintaining the same molarities as previously given, suitable alternate buffers should be utilized. For example, it is known that a citrate buffer (sodium citrate and citric acid) provides a system or gel pH of between about 6.0 and 6.3; a maleic buffer provides a system or gel pH of between about 5.9 and about 6.1; an MES buffer provides a system or gel pH of about 5.9; and a bis-Tris buffer provides a system or gel pH of about 6.4.

It should be appreciated that while each of the individual ingredients referred to above has been previously utilized for electrophoretic separation, the prior art does not teach the specific formulation (combination and/or amount) for any purpose, let alone for the purposes of this invention.

The gel plate is prepared by first forming an homogeneous mixture of the components and thereafter casting the homogeneous mixture on a backing sheet which may be a polyester film such as Mylar manufactured by DuPont. The backing sheet is electrically and chemically inert relative to the electrophoretic process. The homogeneous mixture semi-solidifies with enlarged blocks at either end as set forth in the aforementioned copending application.

The gel plate prepared as just described may be placed in the Helena REP system, human serum samples applied and thereafter the REP system operated at about 1400 volts, for about 12-15 minutes, at about 10° C. to electrophorese the samples. This appears to be an optimal combination of the three known variables of time, temperature and voltage, although many variations will perform successful electrophoretic separation. After the electrophoretic separation, one of several techniques may be employed for both qualitative and quantitative evaluation. For example, electrophoresed samples may be subjected to staining or reagent treatments as are conventional. For CK-MM and CK-MB isoform separation, it appears that routine reagent processing followed by quantitative evaluation under fluorescent light is preferred; such a technique is certainly more convenient than staining.

The present invention provides a new and improved agarose gel formula and method for CK isoform electrophoretic separation. The foregoing is a complete description of the preferred or optimum formula, as well as ranges thereof, for an improved gel formulation and an improved system for electrophoretic separation. The invention should not be limited by the specific data presented because numerous modifications will be apparent to those of ordinary skill in the art. The invention, therefore, should be limited only by the following claims.

What is claimed is:

1. A method for discretely separating CK-isoforms from biological samples comprising the steps of:
   providing an homogeneous mixture of agarose and buffer in the form of a gel having an acidic pH and a molarity from about 0.045M to about 0.055M;
   applying a biological sample containing CK to said gel; and electrophoresing the sample for discretely separating CK into at least two CK-isoforms.

2. The invention as defined in claim 1 wherein the pH of the gel is between about 5.9 and about 6.5.

3. The invention as defined in claim 1 wherein the sample is electrophoresed for separating isoforms of CK-MM.

4. The invention as defined in claim 1 wherein the sample is electrophoresed for separating isoforms of CK-MB.

5. The invention as defined in claim 1 wherein the sample is electrophoresed for separating isoforms of both CK-MM and CK-MB.

6. The invention as defined in claim 1 wherein the electrophoresing takes place at about 1400 volts for about twelve to about fifteen minutes.

7. The invention as defined in claim 1 wherein the electrophoresing takes place at about 10° C.

8. The invention as defined in claim 1 wherein the gel includes at least one additional component selected from the group consisting of humectants, stabilizers and preservatives.

9. The invention as defined in claim 1 wherein the buffer includes at least one of Tris and barbituric acid.

10. The invention as defined in claim 1 wherein the buffer is selected from the group consisting of Tris, bis-Tris, barbituric acid MES and citrate.

11. A method for discretely separating CK-isoforms from biological samples comprising the steps of:

providing an homogeneous mixture of agarose and buffer in the form of a gel having an acidic pH and a molarity from about 0.045M to about 0.055M, the buffer being selected from the group consisting of Tris, bis-Tris, barbituric acid MES and citrate;

applying a biological sample containing CK to said gel; and electrophoresing the sample for discretely separating CK into at least two CK-isoforms.

* * * * *